(12) United States Patent
Yonce

(10) Patent No.: US 10,765,702 B2
(45) Date of Patent: Sep. 8, 2020

(54) VAGINAL LAXITY THERAPY UTILIZING CELL-BASED BULKING COMPOSITIONS

(71) Applicant: Boston Scientific Scimed, Inc., Maple Grove, MN (US)

(72) Inventor: David J. Yonce, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/692,823

(22) Filed: Aug. 31, 2017

(65) Prior Publication Data

US 2018/0008647 A1     Jan. 11, 2018

Related U.S. Application Data (63) Continuation of application No. 14/170,305, filed on Jan. 31, 2014, now Pat. No. 9,775,864.
(Continued)

(51) Int. Cl.
*A61K 35/35*     (2015.01)
*A61K 9/00*     (2006.01)
(Continued)

(52) U.S. Cl.
CPC .............. *A61K 35/35* (2013.01); *A61B 17/00* (2013.01); *A61B 17/42* (2013.01); *A61K 9/0034* (2013.01);
(Continued)

(58) Field of Classification Search
None
See application file for complete search history.

(56) References Cited

U.S. PATENT DOCUMENTS

| 4,669,478 A | 6/1987 | Robertson |
| 5,224,494 A | 7/1993 | Enhorning et al. |

(Continued)

FOREIGN PATENT DOCUMENTS

| WO | 9922680 A1 | 5/1999 |
| WO | 2009120879 A1 | 10/2009 |
| WO | 2011006056 A1 | 1/2011 |

OTHER PUBLICATIONS

Erol et al., Plast. Reconstr. Surg. 121:2127-2133 (2008).*
(Continued)

*Primary Examiner* — Thomas J. Visone
(74) *Attorney, Agent, or Firm* — Brake Hughes Bellermann LLP (57) ABSTRACT

The invention provides methods for the treatment of vaginal laxity which include delivering a cell-containing composition to the vagina. The composition can include fat tissue to provide a bulking effect to reduce the size of the vaginal opening. The cells can provide healing and revascularization of the vaginal treatment area to sustain the bulking provided by the fat. The invention also provides systems and compositions useful for performing the method, and can include instruments and devices for removal of autologous adipose tissue from a patient (e.g., by liposuction), equipment for the enrichment of cells from adipose tissue, mechanical processing of adipose tissue, and the mixing of cells and processed adipose tissue. Devices for the delivery of the cell compositions to the vagina can also be included in the system.

11 Claims, 2 Drawing Sheets

Related U.S. Application Data (60) Provisional application No. 61/759,075, filed on Jan. 31, 2013.

(51) Int. Cl.

| | | |
|---|---|---|
| *A61B 17/42* | (2006.01) | |
| *A61M 31/00* | (2006.01) | |
| *A61L 27/38* | (2006.01) | |
| *A61L 27/54* | (2006.01) | |
| *A61L 29/16* | (2006.01) | |
| *A61B 17/00* | (2006.01) | |
| *A61F 6/08* | (2006.01) | |
| *A61M 25/10* | (2013.01) | |
| *A61M 37/00* | (2006.01) | |

(52) U.S. Cl.
CPC ....... *A61L 27/3834* (2013.01); *A61L 27/3882* (2013.01); *A61L 27/54* (2013.01); *A61L 29/16* (2013.01); *A61M 31/00* (2013.01); *A61F 6/08* (2013.01); *A61K 9/0036* (2013.01); *A61L 2300/414* (2013.01); *A61L 2300/64* (2013.01); *A61L 2400/06* (2013.01); *A61L 2430/22* (2013.01); *A61M 2025/105* (2013.01); *A61M 2037/0023* (2013.01)

(56) References Cited

U.S. PATENT DOCUMENTS

| | | | |
|---|---|---|---|
| 5,269,321 A | 12/1993 | MacDonald et al. | |
| 5,492,532 A * | 2/1996 | Ryan | A61M 25/104 604/103.09 |
| 6,086,909 A | 7/2000 | Harrison et al. | |
| 6,210,392 B1 * | 4/2001 | Vigil | A61M 25/1002 604/103.02 |
| 6,428,467 B1 | 8/2002 | Benderev et al. | |
| 6,428,513 B1 * | 8/2002 | Abrahamson | A61M 25/0097 604/174 |
| 6,638,246 B1 | 10/2003 | Naimark et al. | |
| 6,645,137 B2 | 11/2003 | Ulmsten et al. | |
| 7,049,057 B2 | 5/2006 | Atala et al. | |
| 7,338,468 B2 * | 3/2008 | Freyman | A61M 25/1002 604/103.01 |
| 2001/0007931 A1 * | 7/2001 | Blatter | A61M 25/10 604/103.01 |
| 2002/0182661 A1 | 12/2002 | Kahne et al. | |
| 2004/0013652 A1 * | 1/2004 | Marko | A61K 31/715 424/93.7 |
| 2005/0177100 A1 | 8/2005 | Harper et al. | |
| 2006/0153815 A1 | 7/2006 | Seyda et al. | |
| 2007/0036768 A1 | 2/2007 | Fraser et al. | |
| 2007/0224173 A1 | 9/2007 | Koullick et al. | |
| 2007/0274960 A1 * | 11/2007 | Harman | C12N 5/0667 424/93.7 |
| 2008/0014181 A1 | 1/2008 | Ariff et al. | |
| 2008/0287879 A1 | 11/2008 | Harkins et al. | |
| 2009/0304654 A1 | 12/2009 | Lue et al. | |
| 2011/0008299 A1 | 1/2011 | Koullick et al. | |
| 2012/0253295 A1 * | 10/2012 | Nentwick | A61M 25/0097 604/264 |
| 2012/0259162 A1 | 10/2012 | Karapasha et al. | |
| 2012/0296268 A1 * | 11/2012 | Vlodaver | A61F 11/00 604/43 |

OTHER PUBLICATIONS

Alderman, et al., J. Prolother, 3(3), 2011, pp. 689-708.
Chen, et al., Int. Urogynecol. J., 13, 2002, pp. 80-87.
Dobaria, et al., East Centr. Afr. J. Pharma. Sci, 10, 2007, pp. 3-13.
Furuta, et al., "Advances in the Understanding of Stress Urinary Incontinence and the Promise of Stem-Cell Therapy", Reviews in Urology 9., 2007.
Ho, et al., Obstet. Gynecol., 114(2 Pt 1), 2009, pp. 300-309.
Jack, et al., "Processed Lipoaspirate Cells for Tissue Engineering of the Lower Urinary Tract: Implications for the Treatment of Stress Urinary Incontinence and Bladder Reconstruction", the Journal of Urology 174, 2005, pp. 2041-2045.
Jankowski, et al., "Regenerative Therapy for Stress Urinary Incontinence", Tzu Chi Medical Journal 20, 2008, pp. 169-176.
Lee, et al., "The effects of periurethral muscle-derived stem cell injection on leak point pressure in a rat model of stress urinary incontinence", Int Urogynecol Journal 14, 2003, pp. 31-37.
MacLennan, et al., Brit. J. Ob. Gyn., 107, 2000, pp. 1460-1470.
Rodriguez, et al., PNAS, 103(32), 2006, pp. 12167-12172.
Santarosa, et al., "Periurethral Injection of Autologous Fat for the Treatment of Sphincteric Incontinence", the Journal of Urology 151, 1994, pp. 607- 611.
Zeng, et al. "Treatment of SUI Using Adipose Derived Stem Cells: Restoration of Urethral Function", Program and Abstracts, 2006.
Zuk, et al., "Multilineage Cells from Human Adipose Tissue; Implications for Cell-Based Therapies", Tissue Engineering 7, 2001, pp. 211-228.

\* cited by examiner

Fig. 1

VAGINAL LAXITY THERAPY UTILIZING CELL-BASED BULKING COMPOSITIONS

CROSS-REFERENCE TO RELATED APPLICATIONS

This application is a Continuation of, and claims priority to, U.S. patent application Ser. No. 14/170,305, filed on Jan. 31, 2014, entitled "VAGINAL LAXITY THERAPY UTILIZING CELL-BASED BULKING COMPOSITIONS", now U.S. Pat. No. 9,775,864, which, in turn, claims priority to U.S. Patent Application No. 61/759,075, filed on Jan. 31, 2013, entitled "VAGINAL LAXITY THERAPY UTILIZING CELL-BASED BULKING COMPOSITIONS", the disclosures of which are incorporated by reference herein in their entirety.

BACKGROUND

Vaginal laxity is a condition that affects 20 million women in the U.S. alone, ranging in ages 15-49, and is described as a looseness of the vaginal canal or introitus. This condition is most often caused by trauma from vaginal childbirth delivery and has been identified as a legitimate medical condition by gynecological professionals. Further, most gynecologists identify laxity as the third piece of the triad of vaginal birth defects that also includes urinary incontinence and vaginal prolapse. Physicians have noted that women who develop vaginal laxity will often later go on to develop vaginal prolapse. Of the 20 million women affected by vaginal laxity, approximately half are bothered by it and would like a solution. However, many physicians do not bring it up with their patients because of a lack of treatment options.

SUMMARY

The invention provides systems, methods, and compositions for the treatment of vaginal laxity that include the use of the patient's own autologous tissue. The treatment methods of the invention can also be useful for preventing prolapse, which is thought to follow vaginal laxity later in life if the laxity condition is not treated.

In embodiments, the invention provides a method for treating vaginal laxity. The method comprises a step of providing a composition comprising a patient's autologous tissue and/or cells, and also a step of introducing the composition into the vaginal cavity. The introduced composition can bulk the region and reduce the size of the vaginal opening and cavity, thereby treating the vaginal laxity.

The method can optionally include one or more steps to obtain or prepare the composition comprising the patient's autologous tissue and/or cells. For example, a tissue sample can be obtained from the patient and processed to isolate or enrich cells for the composition. In some cases, the method includes a step of obtaining an adipose tissue sample from the patient, and a step of processing the adipose tissue to isolate or enrich adipose tissue-derived cells, such as adipose tissue-derived stem cells. The method can include steps such as removing the adipose tissue from a patient by liposuction, and using tissue processing equipment to isolate or enrich the adipose tissue-derived cells.

The method can optionally include one or more steps of culturing the patient's autologous tissue and/or cells in vitro to promote differentiation towards a desired cellular phenotype, such as vaginal epithelial cells or vaginal muscle cells. Stimulated autologous cells, in a pre-differentiated state, or in a differentiated state, can be delivered to the vaginal cavity. Optionally, the cells can be delivered to the vaginal cavity along with a cellular matrix used for cell culturing.

The composition can also include one or more components in addition to the patient's autologous tissue cells. For example, the composition can further include the patient's fat, growth factors, or combinations thereof. In these embodiments the method can optionally include the steps of processing adipose tissue sample from the patient (e.g., by mechanical action processing), and then mixing the processed adipose tissue with isolated or enriched adipose tissue-derived cells. In other embodiments the method further includes mixing one or more growth factors with the cells, or with a mixture of cells and processed adipose tissue. The growth factors can be obtained from the patient's tissue, or can be obtained from a different source.

If a composition including processed adipose tissue is used, the processed adipose tissue in the mixture can act as the bulking agent, while the cells isolated or can provide healing and revascularization of the vaginal treatment area to sustain the bulking provided by the processed adipose tissue. Further, the composition can include immune factors in mixture with adipose-derived stem cells that that can promote differentiation of stem cells into muscle cells. Differentiation of the stem cells can lead to strengthening the musculature of the vaginal area and reduce the risk of, or prevent prolapse later in life.

The invention also provides systems for treating vaginal laxity. In some embodiments the system comprises a composition comprising a patient's autologous tissue cells, and a device for delivering the composition to the vaginal cavity. The device can be one that is insertable into the vagina (such as a pessary) that can facilitate desired release of the cells. In other embodiments the system comprises equipment for providing a composition comprising a patient's autologous tissue or cells. Such equipment can include one or more instruments for obtaining a tissue sample (e.g., adipose tissue) from the patient, such as liposuction instruments; a device for enriching cells from the tissue sample; a device for mechanically processing tissue (e.g., adipose tissue); or combinations thereof.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Women having vaginal laxity ("vaginal looseness") can have symptoms, issues, and/or experiences such as discomfort and characteristics of prolapse, tampons falling out of the vagina, lack of friction during intercourse, penis falling out of vagina during intercourse, vaginal wind, and bathwater entrapment (e.g., see Textbook of Female Urology and Urogynecology, 2nd Edition (2006); Cardozo, L., and Staskin, D., eds.; Informa Healthcare, UK). A healthcare professional, such as a gynecologist, can diagnose a female with vaginal laxity based on some or all of these conditions.

Embodiments of the invention include those directed to compositions, systems, and methods for the treatment of vaginal laxity.

Anatomically, the vagina is a muscular orifice having a partially collapsed tubular shape, extending from the vestibule of the vulva to the uterus. The depth of the adult vagina is approximately 4 1 h to 5 inches. The vagina has anterior and posterior walls that are contact with one another, except at the apex where the vagina surrounds the ectocervix. Fornices (vault-like recesses) divide the vagina and cervix. The anterior fornix is shallower than the posterior fornix. Anterior to the vagina are the urethra and the neck of the bladder. The rectum is posterior to the vagina.

The vagina is lined with stratified squamous epithelium and has crypts (anatomical invaginations into the cellular layer) that produce mucus. Mucus production prevents bacteria from entering the uterus and also aids in reproduction when sperm enters the uterus. The superficial layer of vaginal tissue is not keratinized. Microorganisms common to the adult vagina include Doderlein bacilli, diphtheroides, and anaerobic streptococci. The microorganism flora produces lactic acid from glycogen made by the vaginal cells. This provides the vagina with a low pH and enhances normal secretions.

Hormones can act upon the vaginal epithelium. Proliferation and maturation of the epithelium is caused by estrogen action on the tissue, with glycogen accumulating in the epithelial cells.

The term "autologous" refers to material that is obtained from the same individual. Autologous tissue and autologous cells are those tissues and cells obtained from, for example, the same patient. Therefore, a treatment that uses autologous cells can be one where an adipose tissue sample is taken from a patient, the patient's autologous cells are obtained from the adipose tissue sample, and then autologous cells are reintroduced into the patient in a desired manner.

In some modes of practice, the composition comprising a patient's autologous tissue and/or cells is prepared from an adipose tissue sample from the patient. In some modes of practice, adipose tissue is removed from a desired anatomical location in the patient, processed to provide a composition, and then the composition is introduced into the vaginal cavity. Optionally, the composition is cultured before being introduced into the vaginal cavity. The introduced composition can bulk the region and reduce the size of the vaginal opening and cavity, thereby treating the vaginal laxity. Processed adipose tissue in the composition can act as the bulking agent. In other embodiments a bulking agent that is different than processed adipose tissue can be used. Enriched or isolated cells mixed back in with the processed adipose tissue can sustain the bulking provided by the fat. For example, the isolated cells can support formation of tissue by providing effects of healing and revascularization of the vaginal treatment area.

Adipose tissue (i.e., fat) includes or yields a high number of desirable cell types, including stem cells, which can be enriched from the tissue and reintroduced into the patient for revascularization. Adipose tissue can also be disaggregated and used as a bulking composition. Disaggregated adipose tissue, and cells (e.g., stem cells) enriched or purified from the adipose tissue can be mixed together and used as the composition for introduction into the vaginal cavity. For example, in preparing the composition, an adipose tissue sample can be obtained and separated into first and second portions. Cells such as stem cells can be enriched or purified from the first portion. Adipose tissue from the second portion can be disaggregated by mechanical action, such as chopping. Cells enriched from the first portion can then be mixed with disaggregated adipose tissue from the second portion.

To obtain an adipose tissue sample, a lipectomy surgical procedure can be performed. As a general matter, during lipectomy fat is removed from an area in the body using a thin metal suction tube introduced through a skin incision. The tube is repetitively moved through the tissue to break up the fat globules. Vacuum is applied to remove the loosened fat globules. A medical instrument for performing lipectomy may have a hollow body that can be grasped with the hand. At one end, a suction probe is attached to the body and the other end of the body is connected to a source of vacuum. The probe is used to break the fat globules and then suction is applied to suck the loosened fat globules out of the body. The process is repeated until a desired amount of fat is withdrawn from the body. Lipectomy methods and instruments are known in the art. For example, see U.S. Pat. Nos. 4,568,332, 5,013,300, and 5,665,101.

Adipose tissue obtained by lipectomy can be processed and the cell preparation obtained can be mixed with disaggregated adipose tissue and reintroduced into the vagina of the same patient, thereby providing an autologous source of cells.

The adipose tissue can come from anywhere in the body. In one embodiment, the adipose tissue is obtained from the abdominal area of the patient. Other common areas may include the thigh and back area of the patient. In some modes of practice, to provide an amount of composition for introduction into the vagina for treatment of vaginal laxity, adipose tissue in an amount in the range of about 50 cc to about 200 cc is obtained from the patient. In some modes of practice, the adipose tissue can then be separated into two (or more) portions, one for preparing the enriched cell population, and the other for preparing the disaggregated adipose tissue which can serve as the bulking agent as well as the "cell matrix" for the enriched population of cells.

In some modes of practice, adipose tissue is processed to separate the adipose-derived stem cells from the other material including other cellular and non-cellular material in the adipose tissue. Preparation methods can include steps of washing the tissue, treating the tissue with collagenase or trypsin, or optionally with mechanical agitation. Liposomes, which are generally aggregated, can be separated from free stromal cells which include the stem cells and other cells such as red blood cells endothelial cells, and fibroblast cells, by centrifugation. Erythrocytes can be lysed from the suspended pellet and the remaining cells can be filtered or centrifuged. Optionally, cells may be separated by cell sorting or separated immunohistochemically. Methods for the preparation of adipose-derived stem cells are described in commonly-assigned application number WO 2009/120879.

In other modes of practice, the adipose tissue is processed to remove partially or substantially non-cellular components, and to form a heterogenous cell mixture. The heterogenous cell mixture can include endothelial cells, endothelial precursors and progenitors, mesenchymal stem cells, vascular smooth muscle cells, fibroblasts, pericytes, macrophages, and the like.

PCT Application PCT/US2010/041508 describes methods and apparatus for the preparation of cellular material. The methods and apparatus can be used in the method and systems of the current invention. Cell separation equipment is also commercially available from, for example, Tissue Genesis, Inc. (Honolulu, Hi.).

In some modes of practice tissue derived (e.g., adipose-derived) autologous stem cells can be treated to induce their differentiation towards a desired cell type. After obtaining from a patient, the sample of autologous cells including stem cells can be placed in a cell culture environment in contact with a cell differentiation factor for a period of time. The period of time can be minutes, hours, days, or weeks, depending on desired stimulatory parameters for cell differentiation. The cells can be placed in a desired cell culture container to promote differentiation and optionally expansion. Examples of cell culture containers include flasks, dishes, plates, and multi-well plates.

In this case, the liposuction procedure, cell enrichment, cell culturing, and reintroduction into a patient may be performed in a single clinic or hospital visit. Culturing in this mode of practice may be carried out over a short period of time, such as on the order of minutes of hours. In other cases, cell culturing may be performed over the course of a day or days, or weeks. In these scenarios, the patient may have two or more office clinic or hospital visit. For example, a first visit to perform the liposuction procedure and begin the cell enrichment and cell culturing procedures, and a second visit to introduce the cultured cells into the patient.

In vitro culturing can include use of cell scaffolds to promote differentiation and growth of the cells. Exemplary scaffolds include degradable materials and non-degradable materials. Exemplary non-degradable (which otherwise may be referred to as biostable, non-absorbable) materials include, but are not limited to poly(vinylchloride), polystyrene, poly(vinylidene fluoride), poly(vinylidene chloride), polymethylmethacrylate (or other acrylic resins), polyamide, polyester, polyarylene oxide, polysulfone, polyethylene, polypropylene, and polyvinyl alcohol. Cultured cells can be separated from the non-degradable materials prior to reintroduction in the body.

Exemplary degradable (e.g., bioabsorbable) materials include degradable aliphatic polyesters such as polylactic acid, poly(lactide-co-glycolide), polycaprolactone, poly (valerolactone), poly(glycolic acid), poly(glycolide), and poly(dioxanone); polyhydroxyalkanoates, such as poly-4-hydroxybutyrate (P4HB), poly(3-hydroxyvalerate, and poly (hydroxybutyrate-co-hydroxyvalerate); polyorthoesters; polyalkeneanhydrides, such as poly(sebacic acid); polyanhydrides, polyphosphazine; and natural degradable polymers such as hyaluronic acid, alginate, dextran, cellulose, xanthan, pullulan, chitosan, pectin, and inulin. Cultured cells can be separated from the degradable materials prior to reintroduction in the body, or can be left in contact with the degradable materials as they will be absorbed by the body after a period of time following cell delivery.

The cells can be cultured on a scaffold that includes one or more extracellular matrix (ECM) component(s). ECM components include fibrous proteins such as collagen; elastic proteins such as elastin; glycoproteins such as fibronectin; and binding proteins such as laminin; glycosaminoglycans heparin sulfate, chondroitin sulfate, keratan sulfate, and hyaluronic acid. Cellular scaffolds including ECM components are commercially available (e.g., BD Matrigel™ Basement Membrane Matrix, which is a solubilized basement membrane preparation including laminin, collagen IV, heparan sulfate proteoglycans, and entactin/nidogen. Matrigel™ also contains TGF-beta, epidermal growth factor, insulin-like growth factor, fibroblast growth factor, tissue plasminogen activator, 3,4 and other growth factors which occur naturally in the EHS tumor.)

If a scaffold is used to culture cells it can include the polymer material (e.g., either biostable or biodegradable) in a fine fibrous form. Fine fibers of polymeric material for a cell scaffold can be prepared using an electrospinning process. Electrospinning uses an electric field to during the formation of the polymeric fibers. Exemplary electrospinning processes are described in U.S. Pat. No. 6,743,273 and U.S. Publication No. 2006/0290031.

Fine fiber scaffolds can have directed or random orientations, and optionally be layered. The fine fiber scaffolds can have very small spaces (e.g., pores) between the fibers that can permit the penetration and in-growth of cells and that also ready permit diffusion of cell culture materials such as liquids, ions, proteins, and active factors in and out of the scaffold.

Other fine fiber processing techniques include polymer extrusion. An exemplary fine fiber polymer scaffold is formed from extruded polyglycolic acid (PGA). For example, Freed L. E., et al. (Biotechnology (N.Y) 199412: 689-93) describes the extrusion and orientation of micron-sized PGA fibers. Textile processing techniques can be used to produce fibrous scaffolds with a high porosity percentage and good structural integrity. Degradable fibers can optionally be introduced into the body along with the autologous cells, as the fibers will eventually be broken down and absorbed by the body. The fibers can also induce cell differentiation with respect to morphology and phenotype.

In some modes of practice, the cells seeded on a biodegradable scaffold, and then the cell scaffold is placed within the vaginal cavity of the patient in need of treatment. The cell scaffold can be cultured for a desired period of time prior to placing in the patient. The cell scaffold can also be configured for placement within the confines of the vaginal cavity. For example, the scaffold can be cut to provide a desired shape of material appropriate for contact with a vaginal wall of the cavity.

The cell scaffold can also be associated with an article configured for insertion into the vagina, such as a pessary, tampon, vaginal ring, suppository, or vaginal sponge. For example, the cell scaffold is in the form of a layer on the article (e.g., pessary) surface. The article may have multiple layers of biodegradable cell scaffolding on its surface. In use, the biodegradable scaffolding can degrade over a period of time and transfer the cells therein to the vaginal tissue in need of treatment. Exemplary pessaries are described in U.S. Pat. Nos. 3,554,184, 5,224,494, 6,158,435, 6,428,467, and 6,645,137.

As used herein, a "differentiation factor" refers to a molecule having bioactivity capable of causing cellular differentiation. Cell differentiation refers to a process of a generic cell (e.g., non-specific) developing into one that is more specific. For example, a differentiation factor can act on a totipotent cell or pluripotent cell to develop the cell into a certain cell type. Proliferation of the cell can also occur during cell differentiation. The term "growth factor" as used herein refers a molecule having bioactivity capable of causing the cell or tissue proliferation. A growth factor can act on an undifferentiated cell or a differentiated cell to cause their proliferation. In many cases the growth factor can also cause cell differentiation.

Exemplary growth and/or differentiation factors include transforming growth factor-alpha (TGF-a); transforming growth factor-beta (TGF-p), including TGF-p1, TGFp2, and TGF-P3; colony stimulating factor (CSF), such as granulocyte-CSF, macrophage-CSF, granulocyte-macrophage-CSF; platelet-derived growth factors (PDGF) such as PDGF-AA, PDGF-AB and PDGF-BB isoforms; nerve growth factor (NGF) such as NGF 2.5s, NGF 7.0s, and P-NGF; neurotrophins and brain derived neurotrophic factor; fibroblast growth factor (FGF) such as FGF acidic isoforms 1 and 2, FGF basic form 2, and FGF 4, 8, 9 and 10; vascular endothelial growth factor (VEGF), EG-VEGF, VEGF-related protein, Bv8, and VEGF-E; insulin like growth factor (IGF) I and II; cartilage derived factor; bone growth factor (BGF); erythropoietin; IL-3; hepatocyte growth factor; glial neurotrophic growth factor (GDNF), stem cell factor (SCF), keratinocyte growth factor (KGF); skeletal growth factor; bone matrix derived growth factors, and bone derived growth factors and mixtures thereof.

In some mode of practice, the cells can be cultured with one or more growth and/or differentiation factor(s) prior to delivering the stimulated cells to the vaginal cavity. In other modes of practice, the cells are contacted with the one or more growth and/or differentiation factor(s) while the cells are being delivered to the vaginal cavity, or after the cells have been delivered to the vaginal cavity.

During in vitro cell culturing, or in vivo seeding, the composition can include use of one or more cell attachment factors. Cell attachment and differentiation to a desired phenotype can be promoted by using an ECM factor such as collagen, fibronectin, laminin, or a glycosaminoglycan (e.g., keratin sulfate, heparan sulfate, chondroitin, dermatan sulfate). Peptides with active motifs for cell attachment can also be used. Other components useful for cell attachment include agar, agarose, gelatin, gum arabic. Cell attachment factors can be associated with a cell scaffold for in vitro culturing. In another mode of practice the cell attachment factor is provided to the vaginal cavity before or during introduction (or both) of the autologous cells in order to promote cell attachment to the existing vaginal tissue of the patient.

Stem cells that have been induced to differentiate towards a vaginal cell type, such as vaginal epithelial cells or vaginal muscle cells can optionally be monitored in vitro or in vivo to assess differentiation towards the desired phenotype.

The term "vaginal epithelial cells" are those cells that have characteristics of epithelial cells native to the female vagina. Vaginal epithelial cells include cell types of parabasal epithelial cells, intermediate epithelial cells, and superficial cells epithelial cells. Parabasal cells are the smallest epithelial cells, have a round shape, and a high nuclear to cytoplasmic ratio. Intermediate cells typically have a diameter two to three times that of parabasal cells. Intermediate cells can be subclassified into small intermediate cells, having round or oval shapes and large distinct nuclei, and large intermediate cells having polygonal shape with a low nuclear to cytoplasmic ratio. Superficial cells are the largest vaginal epithelial cells, are polygonal in shape and noticeably flat, and do not have an observable nuclei or have a nuclei that is pyknotic (very small and dark). The term "fully comified" refers to superficial cells lacking nuclei. Some vaginal epithelial cells can also be described as "squamous," as present in squamous epithelium which is characterized by a superficial layer wherein the cells are flat, scale-like. Vaginal epithelial cells can also include endometrial cells.

Vaginal epithelial cells can also be characterized by the presence of certain biomolecular marker on the surface of the cells, or within the cells. Stem cells may differentiate towards a vaginal epithelial cell type that present a cytokeratin marker. For example, the epithelial cells can be examined for the presence of cytokeratin intermediate filaments (e.g., see, Classen-Linke et al. (1997) Cell Tissue Res. 287: 171-185) which is often used for characterization. Vaginal epithelial cells can be identified or characterized using monoclonal anti-pancytokeratins AE1/AE3, which bind to many acidic and basic cytokeratin proteins. Cytokeratins are intermediate filament proteins part of the cytoskeletal componentry.

The AE3 monoclonal antibody recognizes the 65 to 67 triplet, 64, 59, 58, 56, and 52 kD proteins also known as cytokeratin 1, 2, 3, 4, 5, 6, 7, while the AE1 antibody recognizes 56.5, 50, 50', 48, and 40 kDa proteins (also known as CKIO, 14, 15, 16 and 19). Anti-cytokeratin antibodies are commercially available from, for example, eBioscience, Inc. (San Diego, Calif.).

Vaginal epithelial cells also have a relatively high intracellular glycogen concentration. Lugol staining, which uses iodine and potassium iodide, can be used for detection of vaginal epithelial cells in previously existing or newly formed vaginal tissue (e.g., see, Cibas and Ducatman (2009) Cytology; Chapter 1: Cervical and Vaginal Cytology, Saunders). Other epithelial markers include progesterone receptors, and estrogen receptors (Cooke et al. (1986) Proc. Natl. Acad. Sci. USA 83:2109-2113).

Functionally, vaginal epithelial cells include receptors, signal transduction mechanisms, and cytokine secretion capabilities for promoting host defenses against various microorganism infections.

Following a period of in vitro culturing, or a period of in vivo implantation, adipose derived stem cells that have been promoted to differentiate into vaginal epithelial cells can be tested for the presence of one or more vaginal epithelial cell markers. Vaginal epithelial cells differentiated from adipose stem cells can be described in terms of one or more of these markers.

Vaginal smooth muscle cells can be detected using various techniques, such as by immunostaining with antibodies against alpha smooth muscle actin. Smooth muscle cells can also have prostaglandin E and beta-adrenergic receptors which can trigger increased intracellular cAMP synthesis in response to PGEI (or isoproterenol). Smooth muscle cells can also display enhanced intracellular cGMP synthesis and accumulation when treated with a nitric oxide donor in the presence of a PDE type 5 inhibitor.

Vaginal epithelial or muscle cells can be characterized using cell specific antibodies, such as anti-cytokeratin or anti-smooth muscle a-actin antibodies. In some forms, Western blot analysis can be used to detect protein expression in a cell sample (e.g., from either in vitro culture or from a sample taken from the body) to confirm differentiation into epithelial and smooth muscle cell lines. Tissue sample explanted from the patient following treatment can also be examined for the presence of epithelial cells and/or muscle cells from the newly-formed vaginal tissue. In some cases, formalin-fixed paraffin-embedded tissues can be prepared and stained with antibodies to determine the presence of epithelial cells and/or muscle cells.

During in vitro cell culturing, or in vivo seeding, autologous stem cells can differentiate to cells suitable for forming female vaginal tissue having structures and morphology of native vaginal tissue. The formed tissue can have a physiology that resembles that of normal female reproductive tissue, such as being responsive to hormones and sensory stimulation similar to a normal vagina. Estrogen stimulates the proliferation and maturation of the vaginal epithelium while progestogens inhibit maturation of the epithelium. As another functional property, vaginal cells derived from the stem cells can be capable of producing mucus.

Optionally, newly formed vaginal tissue can be tested for its ability to produce contractile forces (like native vaginal tissue) following electrical stimulation. Following stimulation, functioning vaginal tissue can be characterized by cell depolarization and the release of intracellular cations resulting in a contractile force. Other characteristics include a response to stimulation using a muscarinic or an adrenergic agonists, suggesting the presence of neurotransmitter function.

The cell composition delivered to the vaginal cavity can also promote angiogenesis or neovascularization. Angiogenesis is a process of new blood vessel development and plays an important role in the female reproductive cycle e.g., ovulation, menstruation and placental development. The endothelial cell population can be used to stimulate vascularization. The cells can be treated with a factor that promotes angiogenesis, such as VEGF-C, which is implicated in angiogenesis. (Yancopoulos, G. D., et al. (2000) Nature, 407:242-248. After a period of treatment, newly formed vaginal tissue can optionally be analyzed for the formation of new blood vessels.

In some modes of practice after a population of the adipose-derived cells (e.g., stem cells; ADS Cs) is enriched, the cells can be introduced into the vagina. As discussed herein, the stem cells can optionally be cultured prior to introducing into the vaginal cavity.

In other modes of practice, the adipose-derived cells are mixed with the disaggregated adipose tissue to form a composition which is then introduced into the vagina. The adipose tissue can be disaggregated by mechanical force, such as by cutting, chopping, or mincing the adipose tissue. Generally, during preparation using mechanical action, collagenase or trypsin (enzymatic) digestion is not performed to maintain scaffolding and structured features of the adipose tissue. Adipose particles generated using such a process can be sized for delivery into the vagina. Grinding and filtering parameters can also be employed depending on the particular treatment site needs.

In some preparations, the isolated or enriched cells are mixed with the disaggregated adipose tissue at a weight ratio in the range of about 1:1 to about 1:4 (cells: tissue). Methods for the preparation of an adipose tissue-derived scaffolding for cells are described in commonly assigned International Application PCT/US2009/038426 (WO2009/120879), and are described further herein with reference to the multi-chamber mixing and delivery systems.

Systems and methods of the invention can also include devices, tools, and methods for the preparation of a composition containing a cell population derived from adipose tissue.

The cell containing composition for introduction into the vagina can be of a desired volume based on factors such as the size of the treatment area, and the method and apparatus used to deliver the composition. A single injection can be used to deliver the composition to the vagina, or introduction of the composition can occur over multiple injections or introductions.

The cell-containing composition can optionally include biologics or drugs which can enhance the effectiveness of the cells following injection into the vagina, or that can further improve the condition of the tissue. Optionally, the cell-containing composition can include excipients, additives, or auxiliary substances useful in the vagina.

Multi-chamber mixing and delivery systems can be used to prepare cell-containing compositions, such as ADSC compositions, for introduction into vagina. The devices can also be used for the injection process. Mixing and delivery systems can include various components and elements to facilitate mixing, digesting, filtering and introduction of cellular mixtures, e.g., cells and autologous adipose tissue or scaffolding material, into the vagina for treatment of vaginal laxity. The various components of the systems can be constructed of materials such as polymers, metals, and other like materials compatible for use with such injection systems and methods.

Devices, methods, and compositions prepared therefrom, including those disclosed in U.S. Patent Publication Nos. 2005/0177100, 2006/0100590, 2007/0224173, 2008/0014181, 2008/0287879 and 2009/0018496; U.S. Pat. No. 7,101,354; and PCT International Patent Publication No. WO2008/091251 can be used are envisioned for use in the systems and methods of the current invention, and their disclosures are incorporated herein by reference in their entirety.

The system of the invention can include an injection device, and optionally one or more components for the removal of adipose tissue, the enrichment of adipose derived stem cells, and/or the mixing of enriched or isolated adipose stem cells with a mechanically processed adipose tissue. Other system components which can optionally be incorporated in optional steps of the invention include anesthetics and antibiotics; surgical instruments such as scalpels, forceps, needles, and sutures; and bandages and tapes. The optional components can be used to numb, prevent infection, and/or repair tissue in the patient. Tissue sites affected by treatment or surgical intervention include the vagina and a tissue site from which adipose tissue can be removed from the patient, such as the abdomen.

Introduction of the composition into the vagina can be carried out using any suitable delivery conduit, such as a needle, trocar, cannula, catheter, or other tube or hollowed cylindrical article. For example, a syringe and needle combination can be used to control the flow of the composition manually (i.e., with forces from the hand) by a practitioner during administration.

In some modes of practice, the composition is injected into the vagina using high pressure injection. Use of an injection device that includes a pump to generate the high pressure is one technique for carrying out the collagenase injection. In some arrangements, the injection device can include multiple ports or multiple needles to push the composition out at a fast rate into the vagina. The process of high pressure injection may be referred to as 'jet injection." Device embodiments for introducing the composition can include multiple apertures or multiple needles such as an extended, expanded, or extendable chain, string, array, or sequence (e.g., "daisy chain"). Apertures may be located at an extension mechanism ("aperture extension") such as extendable or fanning needles.

The pressurized fluid source can include a source of fluid and a source of pressure. The pressure source can include a mechanical feature (such as a spring), a pneumatic feature, a hydraulic feature, or an electric feature, etc., to generate the fluid pressure. Further, the pressure source may be mechanically or electronically controlled. The pressure source can cause a fluid contained in a fixed or variable volume chamber to be pressurized to a transient pressure, at the injection orifice, that is sufficiently high to allow the fluid to be ejected from the injection orifice with sufficient force to penetrate the vaginal tissue.

Various device structures, components, methods and techniques described and depicted in U.S. Patent Publication No. 2006/0129125 and International Publication No. WO2007/079152 are envisioned for use, alone or in combination, with the present invention.

The composition can optionally be delivered through an article configured for insertion into the vagina, such as a pessary, balloon device, or vaginal ring capable of receiving and distributing the cell containing composition in the vagina. The article can be of any shape and size suitable for insertion into the vagina and delivery.

For example, the article can receive the cell composition from an external source, and then distribute the composition intravaginally. The distribution of the cell composition can occur by the composition moving from an internal portion of the article, through one or more apertures or openings in an outer material of the article, and out to the vaginal tissue where it is desired for the cells of the composition to seed and generate new vaginal tissue.

In one arrangement, the composition is introduced into the vagina using a balloon-based injection system. For example, a balloon is inflated in the vagina or the site of laxity. The balloon contains fluid pathways and/or micro-needles along the surface to provide a quick and homogeneous injection into the vaginal wall. The balloon can be attached to a distal end of a catheter tube that is in fluid communication with the inflation lumen. The proximal end of the catheter tube can have features for controlling movement of the catheter and balloon during insertion, and controlling inflation of the balloon.

Figure 1:
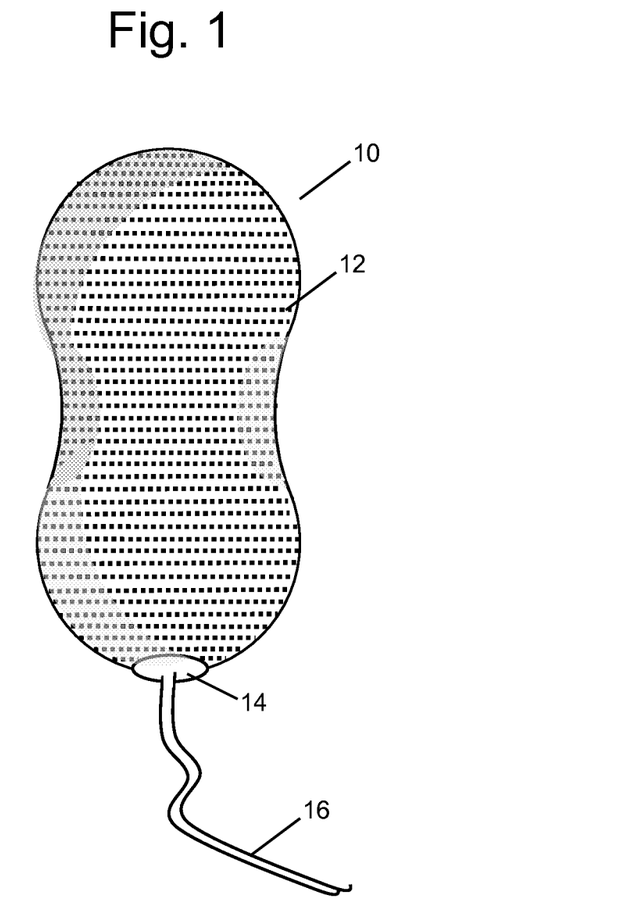
FIG. 1 illustrates a pessary for delivering a cell composition to the vaginal tissue.

In a similar arrangement, the article can be constructed to have an inner space capable of receiving the cell composition, and a wall or membrane that can contact a vaginal wall, and having openings through which the cell composition can flow through. FIG. 1 shows a pessary 10 that is capable of delivering a cell composition to the vaginal tissue having a plurality of openings 12 in its outer wall. Preferably the material of the outer wall is pliable to it can change in shape and/or size, such as during insertion into the vagina, or removal therefrom, during delivery and release of the cell composition, and also after growth of tissue in the vagina. The outer wall can be constructed from a biocompatible and non-absorbable material, such as silicone rubber, nylon, polytetrafluoroethylene (PTFE), a polyamide resin, polyesters, or organosiloxanes.

The apertures in the wall of the article can be sized to allow the passage of cells from the inner space out to the vaginal tissue. For example, the apertures can have a diameter of at least 25 or more preferably, greater than 50 or greater than 100 such as in the range of about 100 µm to about 1 mm or 2 mm. The apertures may increase in size upon expansion of the article.

The article 10 can have a portion with a hub 14 connected to a distal end of a tube or conduit 16 that can supply the inner space of the deliver article with the cell composition. A proximal end of the conduit (not shown) can be attached to a reservoir that supplies the cell composition. The reservoir can also provide a source of pressure causing pressurization of the inner space and movement of the cell composition out through the pores.

Figure 2:
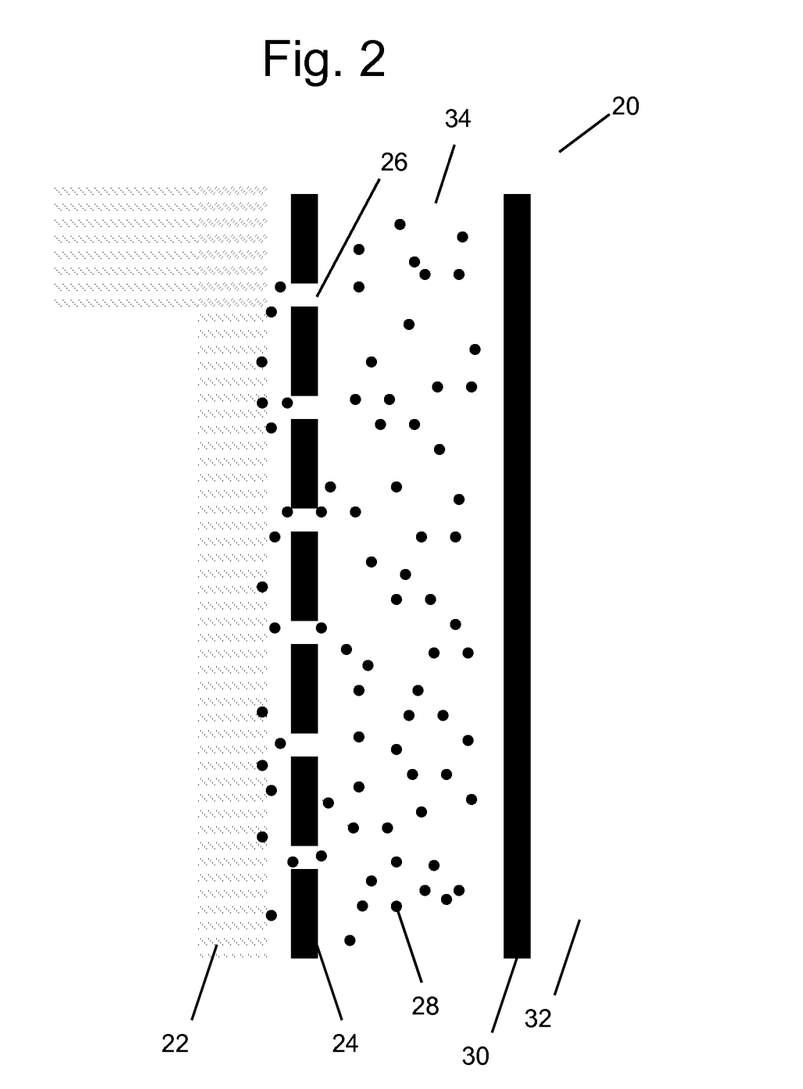
FIG. 2 is a cross-sectional illustration of an article having a double walled structure for delivery of cells to vaginal tissue.

In one arrangement, with reference to FIG. 2, the article 20 can have a double walled structure. FIG. 2 shows a cross-sectional portion of the article, with the outer wall 24 having apertures 26 and an inner wall 30 without apertures. An inner space 34 is defined between outer 24 and inner 30 walls through which a cell-containing composition can flow. For delivery, cells 28 can move through apertures 26 and to the vaginal tissue 22 in which they seed and expand to form new tissue. Inner space 32 represents an area that can be inflated with a liquid or a gas to provide pressure to expand the outer wall to the vaginal tissue and/or cause the flow of the cell containing composition out of the apertures 26.

After delivery of a desired amount of cell composition, the article can be removed from the vagina, or maintained in the vagina. If the article is maintained, the process of cell delivery can be repeated one or more times to provide additional cell composition to the vaginal walls for an increased bulking effect.

Treatment can optionally be carried out using a drug that provides a beneficial therapeutic effect to the vaginal tissue. The drug may be used to enhance the seeding of the autologous cells to the vaginal cavity, to affect newly formed vaginal tissue as a result of the cell seeding, or to provide preventative treatment in order to minimize or eliminate the adverse biological conditions (e.g., such as infection or necrosis). The drug can be orally or locally (i.e., directly into the vaginal cavity) delivered.

In some modes of practice, a steroid drug is administered to the patient before delivery of the cell composition, during delivery of the cell composition, after delivery of the cell composition, or combinations thereof. Exemplary steroid drugs include, but are not limited to an estrogen, such as ethinyl estradiol, 17-estradiol, diethyl stilbesterol, estradiol 3-benzoate, estradiol 17-benzoate, estradiol 17-cyclopentylpropionate, estradiol dipropionate, and ethinyl estradiol. In some modes of practice an anti-inflammatory drug is delivered before, during, after, or combinations thereof. Exemplary anti-inflammatories include triamcinolone, prednisolone, hydrocortisone, cortisone, dexamethasone, and fludinolone. In some modes of practice an antibiotic or antimicrobial is delivered before, during, after, or combinations thereof. Exemplary antibiotics and antimicrobials include erythromycin, penicillin, tetracycline, miconazole, bacitracin, and nystatin. In some modes of practice a progestogen is delivered before, during, after, or combinations thereof. Exemplary progestogens include progesterone, norethynodrel, norethindrone, megestrol, melengestrol, medroxyprogesterone, 19-norprogesterone, and 17-hydroxyprogesterone. In some modes of practice an anti-inflammatory prostaglandins, such as PGE1, PGE2, and PGF2, is delivered before, during, after, or combinations thereof.

What is claimed is:

1. A system for treating vaginal laxity, comprising:
an injection system configured to deliver a composition including adipose tissue cells to a vaginal cavity, the injection system including a balloon that includes an inner wall and an outer wall defining a space therebetween to contain the composition, the balloon including a first end portion and a second end portion and a middle portion between the first end portion and the second end portion, each of the first end portion, the middle portion, and the second end portion includes a plurality of openings to deliver the composition to the vaginal cavity, the injection system configured to reduce a size of the vaginal cavity in response to the delivery of the composition into the vaginal cavity,
the injection system including a tube connected to the balloon to supply the space of the balloon with the composition, a portion of the balloon including a hub member connected to a distal end of the tube.

2. The system of claim 1, wherein the balloon comprises micro-needles.

3. The system of claim 1, further comprising a member for providing the composition including adipose tissue cells of a patient.

4. The system of claim 3, wherein the member comprises a device for enriching cells from the tissue sample.

5. The system of claim 3, wherein the member comprises a device mechanically processing adipose tissue.

6. The system of claim 3, wherein the member comprises a liposuction instrument.

7. The system of claim 1, wherein the inner wall is void of a plurality of openings.

8. The system of claim 1, wherein the space of the balloon is filled with at least one of a liquid or a gas to provide pressure to expand the outer wall of the balloon to a surface of the vaginal cavity.

9. The system of claim 1, wherein the outer wall is constructed from a biocompatible material.

10. The system of claim 1, wherein the outer wall is constructed from a non-absorbable material.

11. The system of claim 1, wherein the outer wall is constructed from at least one of silicone rubber, nylon, polytetrafluoroethylene (PTFE), polyamide resin, polyesters, or organosiloxanes.

* * * * *